United States Patent
Farag et al.

(10) Patent No.: US 11,044,400 B1
(45) Date of Patent: Jun. 22, 2021

(54) FRAME STITCHING IN HUMAN ORAL CAVITY ENVIRONMENT USING INTRAORAL CAMERA

(71) Applicant: Kentucky Imaging Technologies, Louisville, KY (US)

(72) Inventors: Aly Farag, Louisville, KY (US); Mohamad Ghanoum, Louisville, KY (US); Asem Ali, Louisville, KY (US); Salwa Elshazly, Louisville, KY (US)

(73) Assignee: Kentucky Imaging Technologies, Louisville, KY (US)

( * ) Notice: Subject to any disclaimer, the term of this patent is extended or adjusted under 35 U.S.C. 154(b) by 0 days.

(21) Appl. No.: 16/840,035

(22) Filed: Apr. 3, 2020

Related U.S. Application Data

(60) Provisional application No. 62/828,650, filed on Apr. 3, 2019.

(51) Int. Cl.
*G06T 5/50* (2006.01)
*H04N 5/232* (2006.01)
(Continued)

(52) U.S. Cl.
CPC ..... *H04N 5/23238* (2013.01); *A61B 1/00009* (2013.01); *A61B 1/04* (2013.01);
(Continued)

(58) Field of Classification Search
CPC . G06T 7/586; G06T 5/50; G06T 2207/10012; H04N 5/23238; H04N 5/265;
(Continued)

(56) References Cited

U.S. PATENT DOCUMENTS 6,909,913 B2   6/2005   Vining
6,928,314 B1   8/2005   Johnson et al.
(Continued)

OTHER PUBLICATIONS

Mohamed, Mostafa & Farag, Amal & Ali, Asem & Elshazly, Salwa & Farag, Aly & Ghanoum, Mohamad. (2018). Fly-In Visualization for Virtual Colonoscopy. 2062-2066. 10.1109/ICIP.2018.8451412.
(Continued)

*Primary Examiner* — Patrick E Demosky
(74) *Attorney, Agent, or Firm* — Law Office of J. L. Simunic; J. L. Simunic

(57) ABSTRACT

The present invention is a method to stitch images of human teeth that are captured by an intraoral camera. Oral dental applications based on visual data pose various challenges such as low lighting conditions and saliva. Herein we describe a stitching algorithm of low-texture/low-resolution imaging. First, normals of tooth surface are extracted using shape from shading. An algorithm to rectify the imprecise values of the surface normal due to the oral environment is applied and normal maps generated. Second, the normal maps are used to detect, extract and match the corresponding features. Finally, to enhance the stitching process for these unidealized data, normal maps are used to estimate as-projective-as-possible warps. The proposed approach outperforms the state-of-the-art auto-stitching approach and shows a better performance in such cases of low-texture regions.

1 Claim, 2 Drawing Sheets

(51) Int. Cl.
*H04N 5/265* (2006.01)
*A61C 9/00* (2006.01)
*A61C 7/00* (2006.01)
*A61B 1/04* (2006.01)
*A61B 1/24* (2006.01)
*A61B 1/00* (2006.01)
*G06T 7/586* (2017.01)

(52) U.S. Cl.
CPC ............. *A61B 1/24* (2013.01); *A61C 7/002* (2013.01); *A61C 9/0053* (2013.01); *H04N 5/265* (2013.01)

(58) Field of Classification Search
CPC ......... A61B 1/00009; A61B 1/04; A61B 1/24; A61C 7/002; A61C 9/0053
See application file for complete search history.

(56) References Cited

U.S. PATENT DOCUMENTS

| | | | |
|---|---|---|---|
| 7,194,117 B2 | 3/2007 | Kaufman et al. | |
| 7,304,644 B2 | 12/2007 | Geiger | |
| 7,839,402 B2 | 11/2010 | Dekel et al. | |
| 7,853,310 B2 | 12/2010 | Vining et al. | |
| 7,961,187 B2 | 6/2011 | Borland et al. | |
| 8,014,561 B2 | 9/2011 | Farag et al. | |
| 8,041,141 B2 | 10/2011 | Farag et al. | |
| 8,073,226 B2 | 12/2011 | Farag et al. | |
| 8,150,111 B2 | 4/2012 | Borland et al. | |
| 8,259,108 B2 | 9/2012 | Suhling et al. | |
| 9,501,709 B2 | 11/2016 | Ikeda | |
| 9,659,405 B2 | 5/2017 | Wahrenberg | |
| 10,242,488 B1 | 3/2019 | Farag et al. | |
| 10,734,028 B2 | 8/2020 | Fay | |
| 2003/0071194 A1* | 4/2003 | Mueller | H04N 13/221 250/208.1 |
| 2005/0152588 A1 | 7/2005 | Yoshida et al. | |
| 2005/0245803 A1 | 11/2005 | Glenn, Jr. et al. | |
| 2006/0244757 A1* | 11/2006 | Fang | G06T 15/04 345/582 |
| 2007/0003131 A1 | 1/2007 | Kaufman | |
| 2007/0052724 A1 | 3/2007 | Graham et al. | |
| 2008/0055308 A1 | 3/2008 | Dekel et al. | |
| 2008/0118117 A1 | 5/2008 | Gauldie et al. | |
| 2008/0297509 A1 | 12/2008 | Matsumoto | |
| 2009/0016589 A1 | 1/2009 | Wolf et al. | |
| 2013/0127860 A1* | 5/2013 | Hadap | G06T 7/507 345/426 |
| 2013/0286174 A1* | 10/2013 | Urakabe | A61B 1/247 348/66 |
| 2014/0146044 A1 | 5/2014 | Cvetko | |
| 2015/0145966 A1* | 5/2015 | Krieger | G06T 17/20 348/47 |
| 2019/0311461 A1* | 10/2019 | Mercer | G06T 5/50 |

OTHER PUBLICATIONS

M. Mohamad, A. Farag, A. M. Ali, S. Elshazly, A. A. Farag and M. Ghanoum, "Enhancing virtual colonoscopy with a new visualization measure," 2018 IEEE 15th International Symposium on Biomedical Imaging (ISBI 2018), Washington, DC, 2018, pp. 294-297, doi: 10.1109/ISBI.2018.8363577.

\* cited by examiner

FRAME STITCHING IN HUMAN ORAL CAVITY ENVIRONMENT USING INTRAORAL CAMERA

CROSS-REFERENCE TO PRIOR APPLICATIONS

The present application claims priority to U.S. 62/828,650 filed 3 Apr. 2019, which is incorporated herein in its entirety by reference.

FIELD OF THE INVENTION

The present invention is a unique method to stitch images of human teeth that are captured by an intraoral camera. The invention outperforms favorably to existing methods and shows a better performance in such cases of low-texture regions.

BACKGROUND OF THE INVENTION

Along with panoramic radiograph and periodontal checkup, intraoral photos are important visual data for initial diagnosis, treatment planning, active periodontal therapy, reevaluation and maintenance. For example, orthodontic treatment involves the application, over time, of force systems to teeth to correct malocclusion. In order to evaluate tooth movement progress, the orthodontist monitors this movement by means of visual inspection, intra-oral measurements, fabrication of casts, photographs, and radiographs. Therefore, collection of intra-oral images for future treatment is very important. However, dental photography using extra-oral cameras is time consuming and tedious for the patient.

Intra-oral cameras enable dentists to capture images of difficult-to-reach areas in the mouth. These intraoral cameras capture a sequence of calibrated images, i.e., each image captures only a part of the jaw. These images must then be "stitched" together to create one panoramic view of the whole jaw.

There are a variety of approaches to image stitching. Scale Invariant Feature Transform ("SIFT") or Speeded Up Robust Features (SURF) are for extracting key points in these methods. A content-aware warping approach generates rectangular images from stitched panoramic images. Autostitch is a commercially available smartphone app.

The major drawback in most of the existing stitching approaches is that an alignment function is modeled as 2D homographies. But homographies are justified only if the images correspond to views that differ purely by rotation, or if the imaged scene is effectively planar (e.g., when the scene is sufficiently far away). To overcome this limitation, Zaragoza et al. 2014 proposed the Moving Direct Linear Transformation approach for accurate homography estimation that fine-tunes the projective warp to accommodate the deviations of the input data from the idealized conditions.

However, the oral cavity does not allow for images to be captured under ideal conditions. There are often problems with lighting (effect of saliva, tooth discolorization, gum texture, and other sources of specularity) and motion (even inevitable slight motions of the upper/lower jaw may lead to errors far beyond the desired accuracy). Thus, a method is needed to allow for stitching of images obtained under real conditions.

SUMMARY OF THE INVENTION

This present invention addresses two problems: 1) extracting keypoints in a featureless environment, and 2) stitching images captured in non-ideal conditions. The invention is a novel image stitching algorithm to handle the lack of features necessary for establishing region correspondence in a given scene, which is necessary for 3D reconstruction. Normal maps are estimated to reveal the impacted features of teeth surfaces. The as warps are estimated to enhance the stitching process. Results confirm the high performance of the invention.

The present invention can be used under conditions wherein the scene is not rich with features and without the need for devices other than the intra-oral camera and without the need for extra transformation. The invention identifies the required pixel-wise distortion for stitching in contrast to methods of the prior art.

BRIEF DESCRIPTION OF THE DRAWINGS

The application file contains at least one drawing executed in color. Copies of this patent application publication with color drawing(s) will be provided by the Office upon request and payment of the necessary fee.

DETAILED DESCRIPTION OF THE PREFERRED EMBODIMENTS

Figure 1:
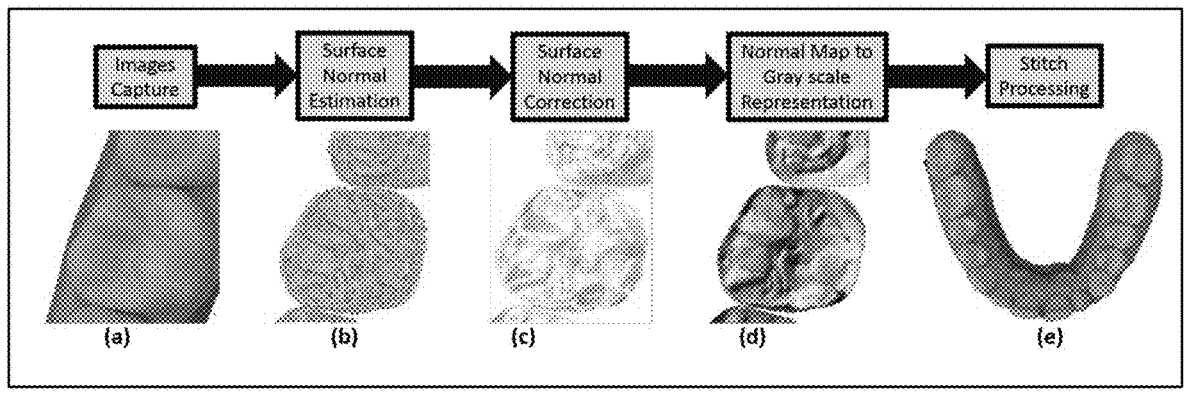
FIG. 1 is a schematic indicating the work flow of the proposed images stitching approach: (a) 2D input image capturing; (b) surface normal extraction; (c) surface normal correction, (d) normal map representation, and (e) image stitching.

The present invention is a unique method to create a 3D reconstruction of a jaw from a plurality of images of human teeth that are captured by an intraoral camera. The method comprises the steps of (1) capturing a plurality of images wherein each image represents a section of the jaw, (2) making a surface normal estimation image for each captured image by extracting the surface normal and using shape from shading; (3) making surface normal corrections using an algorithm to rectify imprecise values impacted by the normal tooth surface, wherein the algorithm corrects a lack of feature region correspondence in a given scene, (4) converting the normal map of images to a gray scale image, and (5) stitching the images together to generate a 3D representative of the jaw. This process, and the images generated at each step in the process, is shown in FIG. 1.

In a preferred embodiment, the intraoral camera is flown in a curve path to capture the images, about 1 cm from the teeth. Up to 100 frames with a resolution 512×512 may be used for a complete 3D reconstruction. The overlap between the images may be above 70% to cover the whole jaw. An example of one frame is shown in FIG. 1(a).

As is known in the art, the surface orientation at a 3D point P in the scene on a surface S is determined by a unit vector perpendicular to the plane tangent to S at P. Shape from Shading (SFS) is an algorithm among the tools used in shape-oriented extraction from a single view. The SFS problem is to find a solution of brightness equation E(x; y)=R(r; q; L) where E(x; y) is the brightness, R(r; q; L) is the surface reflectance map, L is illuminate direction and (r; q) are the surface gradients. Making an assumption of perspective projection and a calibrated camera, a metric representation of teeth and gum surfaces using SFS algorithm is obtained. This approach is used to estimate the surface normal for each captured image. To do this, a unique 3D point P on an object, such as a tooth, is defined by:

$$P = B^{-1}(sp - b) = g(s(x, y)) \qquad \text{Eq. (1)}$$

where B and b are decomposed parameters from the projection matrix, p is the corresponding image coordinate and s is the scalar. Because P equals g(s(x, y)) and the normal at a surface point is defined as N=(r×q)/|r×q| wherein $$r = \frac{dg(s(x, y))}{dx}$$

and $$q = \frac{dg(s(x, y))}{dq},$$

the quantities r and q can be estimated using a Taylor's series expansion and applying the Jacob iterative method, as is known in the art. FIG. 1(b) shows the image of the tooth from the frame of FIG. 1(a) after applying the surface normal estimation.

The oral cavity is an unfriendly environment for image acquisition because it contains several factors that make the quality of the images unrealistic. Hence, the SFS cannot provide accurate information of the surface normals relying upon the raw image information. It is known that the surface normals estimation depends on light direction and the surface patches are homogenous and uniformly lit by distant light source. Assuming that the light and the camera are at the same direction, a light direction vector can be determined. A cross product can then be calculated between the normal surface and the light direction vector. After calculating the cross product, a geometric mean filter with a window size 9 is applied. The technique of geometric mean filtering is known in the art. By applying the cross product as well as the mean filtering, the surface patches, which have the same orientation, have the same surface normal un-like other patches, which are on the border between two planar surfaces. FIG. 1(c) shows the image of the tooth from the frame of FIG. 1(a) after applying the surface normal estimation and the surface normal corrections.

As is known in the art, a normal map is a method to represent the surface normals on the image pixels domain. Each pixel of the map stores the direction of the surface normal at that particular point. Normal maps are commonly stored as regular RGB images where the RGB components correspond to the X, Y, and Z coordinates, respectively, of the surface normal. In the present invention, before mapping each component to its corresponding channel in the image domain, the positive and negative values are compressed into a positive interval [0; 1]. The mapping is done to the red and green channels, $$R = \frac{(\tilde{N}_x + 1)}{2}$$

and $$G = \frac{(\tilde{N}_y + 1)}{2}.$$

Figure 2:
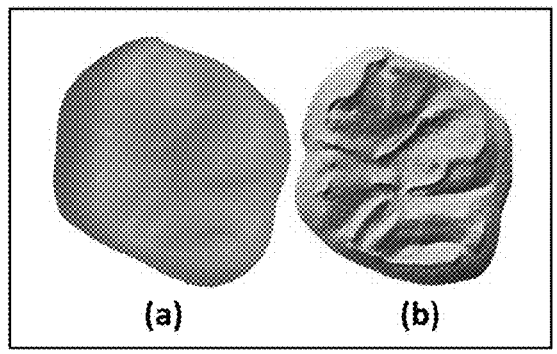
FIG. 2 is a pair of images showing the planar surface segments of a tooth using normal (a) RGB image and (b) the correspondence normal map.

The Z component is always positive, because this is a tangent space normal map, and it is directly mapped to the blue channel. The values $\tilde{N}_x$, and $\tilde{N}_y$ are values of the SFS map in the x- and y-axis, respectively. The value "1" is added to these values to make sure that the mapping is between [0; 1] and the normal map is generated. In the present invention, the RGB normal map is then converted to a gray-scale image, as shown in FIG. 1(d). As is known in the art, the benefit of generating a normal map of an image is to reveal the impacted geometric properties of the images inside an area, boundary, and shape. An example is shown in FIG. 2, wherein the normal map, shown in FIG. 2(b), is rich with of features relative to the captured RGB image, shown in FIG. 2(a).

Features are extracted from the normal map using the KAZE algorithm, a multiscale 2D features detection and description algorithm in nonlinear scale spaces, which uses nonlinear diffusion filtering and makes blurring locally adaptive to the image data with respect to the object boundary and obtaining localization accuracy and distinctiveness.

The prescribed image capturing conditions do not lead to views that differ purely by rotation, nor planar scene since the object is near to the camera. Therefore, using a basic homographic warp yields misalignment. To overcome this problem, we warp each part using a location dependent homography. These estimated as-projective-as-possible warps account for data that deviates from the required constraints. Unlike the prior art, the present invention does not use a uniform grid to partition the image, but rather uses estimated normal maps to segment the 2D domain of the image into connected planar segments. Each pixel is assigned a weight that is inversely proportional to its distance from the centroid of the segment. Then pixels of each planar segment are warped using the same homography. A stitching algorithm is used to merge the separate image reconstructions to generate a 3D reconstruction of the entire oral cavity.

The present invention allows for stitching images captured in non-ideal conditions, i.e. when the intraoral camera movement is not a pure rotation or the camera is far from the teeth. The present invention maintains perspectives in the stitched images for partial or complete 3D reconstruction of the oral cavity, regardless of the occlusions and uncertainties associated with the jaw. The present invention allows for stitching that is more robust than prior art methods and able to accommodate advances in intraoral camera sensors as well as computational shape from shading.

Figure 3:
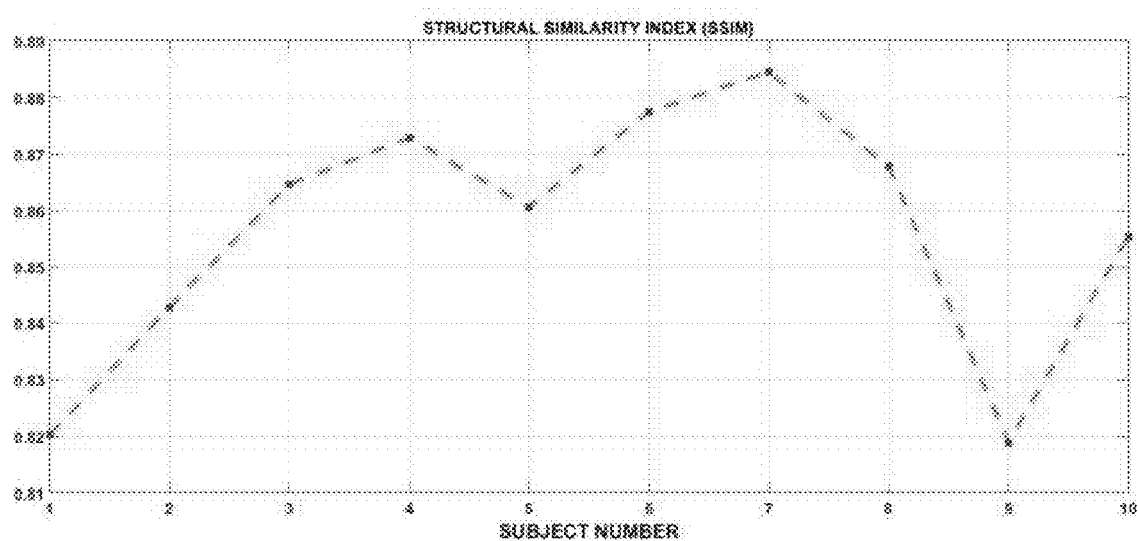
FIG. 3 is a graph showing the structural similarity index metric between the results generated using the present invention and the Ground Truth for ten subjects.
Figure 4:
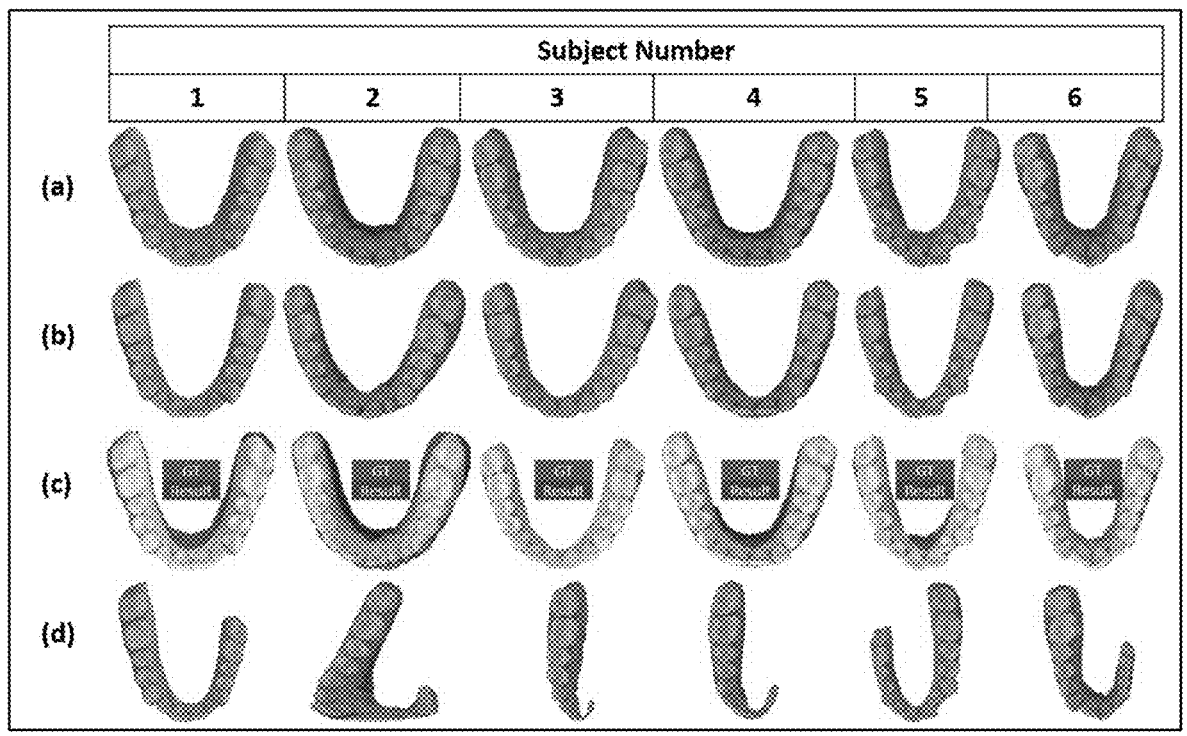
FIG. 4 is a set of images showing examples of different stitching approaches for six different subjects, wherein (a) shows the Ground Truth image for each subject, (b) shows the image using the present invention, (c) shows the alignment of the results generated from the present invention to the Ground Truth image, and (d) shows the results using Autostitching; and, FIG. 5 is a pair of images showing (a) a 3D jaw, and (b) its reconstruction from the generated panoramic image.
Figure 5:
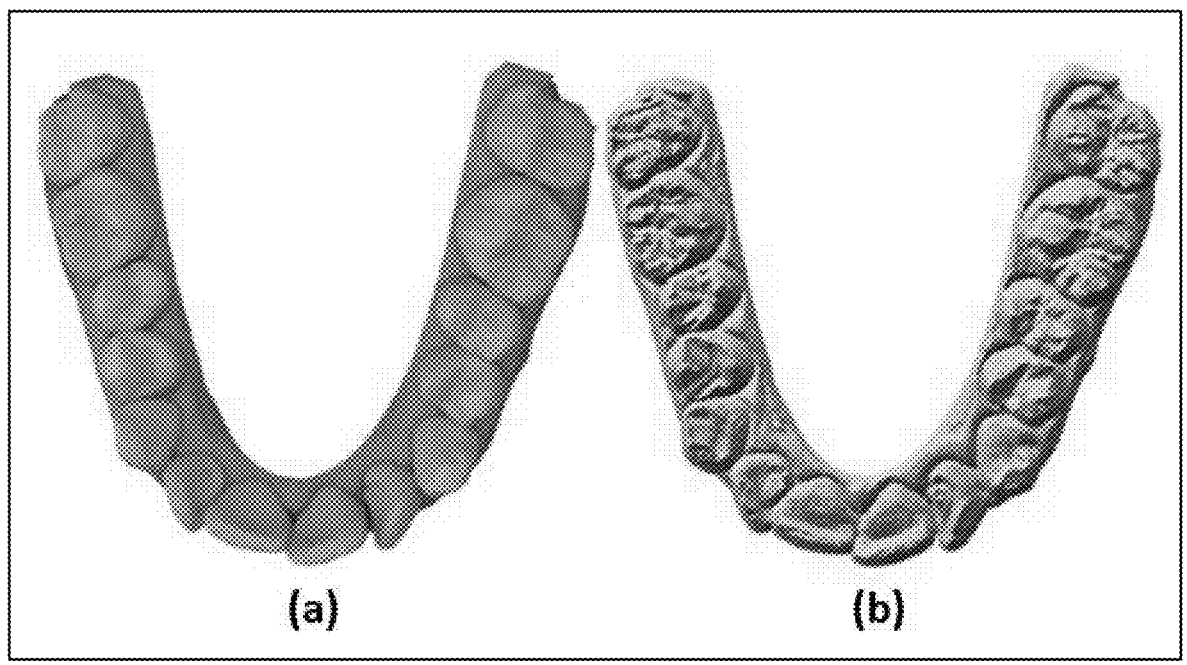

FIGS. 3, 4 and 5 demonstrate the present invention on test subjects. FIG. 3 is graph showing the structural similarity index metric between the results generated using the present invention and the Ground Truth for ten subjects. FIG. 4 is a set of images showing examples of different stitching approaches for six different subjects, wherein (a) shows the Ground Truth image for each subject, (b) shows the image using the present invention, (c) shows the alignment of the results generated from the present invention to the Ground Truth image, and (d) shows the results using Autostitching. FIG. 5 is a pair of images showing (a) a 3D jaw, and (b) its reconstruction from the generated panoramic image.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted. The terms "a", "an", and "the" refer to "one or more" when used in the subject specification, including the claims.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

What is claimed is:

1. A method for generating a panoramic view of a human jaw from a sequence of images that has been obtained from an intraoral camera, the method comprising:

a. capturing a plurality of images from the intraoral camera, wherein each image comprises a plurality of pixels and wherein each image represents a section of the jaw;

b. subjecting the images collected by the camera to algorithmic processing wherein the algorithmic processing comprises the steps of converting data captured by the camera to make a surface normal estimation image for each captured image by extracting a surface normal and using a shape from shading (SFS) algorithm:

c. correcting the surface normal estimations by assuming that the camera and a light source are positioned at the same direction, and then determining a light direction vector, and then calculating a cross product between the surface normal and the light direction vector, and then applying a geometric mean filter to the cross product;

d. using the corrected surface normal estimations to establish an RGB component for each pixel wherein the RGB component defines X, Y and Z coordinates, and wherein the X, Y and Z coordinates may be positive values, negative values or a combination thereof:

e. compressing the positive values and the negative values into a positive interval [0; 1];

f. mapping each RGB component to a respective red channel, green channel and blue channel to produce a normal map of images:

g. converting the normal map of images to a gray scale image, h. using the normal map to segment the image into connected planar segments and then warping pixels of each planar segment into a predetermined location dependent homography; and i. stitching the images together to generate a 3D model representative of the jaw.

\* \* \* \* \*